United States Patent [19]

Harjunmaa et al.

[11] Patent Number: 5,178,142
[45] Date of Patent: Jan. 12, 1993

[54] ELECTROMAGNETIC METHOD AND APPARATUS TO MEASURE CONSTITUENTS OF HUMAN OR ANIMAL TISSUE

[75] Inventors: Hannu Harjunmaa, Holden; Yitzhak Mendelson; Yi Wang, both of Worcester, all of Mass.

[73] Assignee: Vivascan Corporation, Southboro, Mass.

[21] Appl. No.: 725,441

[22] Filed: Jul. 3, 1991

Related U.S. Application Data

[63] Continuation-in-part of Ser. No. 527,514, May 23, 1990, Pat. No. 5,099,123, and a continuation-in-part of Ser. No. 511,229, Apr. 19, 1990, Pat. No. 5,137,023, and a continuation-in-part of Ser. No. 511,341, Apr. 19, 1990, Pat. No. 5,112,124.

[30] Foreign Application Priority Data

May 23, 1989 [EP] European Pat. Off. ........... 89810832

[51] Int. Cl.$^5$ .................... A61B 5/00; G01N 21/59
[52] U.S. Cl. .................................. 128/633; 356/39
[58] Field of Search ................ 128/633–634, 128/664; 356/39, 41; 250/339, 341, 351

[56] References Cited

U.S. PATENT DOCUMENTS

| | | | |
|---|---|---|---|
| 511,229 | 4/1891 | Mendelson et al. | 128/633 |
| 511,341 | 4/1891 | Harjunmaa et al. | 356/39 |
| 527,514 | 5/1890 | Harjunmaa et al. | 250/345 |
| 1,758,088 | 5/1930 | Schmick . | |
| 2,721,942 | 10/1955 | Friel et al. | 250/435 |
| 3,463,142 | 8/1969 | Harte | 128/633 |
| 3,614,450 | 10/1971 | Hill et al. | 250/210 |
| 3,638,640 | 2/1972 | Shaw | 356/41 |
| 3,926,527 | 12/1975 | Pembrook et al. | 356/246 |
| 3,958,560 | 5/1976 | March | 356/39 |
| 3,963,019 | 6/1976 | Quandt | 356/39 |
| 4,029,085 | 6/1977 | DeWitt et al. | 128/2 R |
| 4,033,330 | 7/1977 | Willis et al. | 356/39 |
| 4,169,676 | 10/1979 | Kaiser | 128/633 |
| 4,266,554 | 5/1981 | Hamaguri | 128/633 |
| 4,267,844 | 5/1981 | Yamanishi | 128/633 |
| 4,306,877 | 12/1981 | Lubbers | 23/230 R |
| 4,321,930 | 3/1982 | Jobsis et al. | 128/633 |
| 4,380,240 | 4/1983 | Jobsis et al. | 128/633 |
| 4,398,541 | 8/1983 | Pugliese | 128/665 |
| 4,427,889 | 1/1984 | Muller | 250/339 |
| 4,485,820 | 12/1984 | Flower | 128/633 |
| 4,490,845 | 12/1984 | Steinbruegge et al. | 250/210 |

(List continued on next page.)

FOREIGN PATENT DOCUMENTS

| | | |
|---|---|---|
| 0074428 | 3/1983 | Fed. Rep. of Germany . |
| 0407992 | 1/1991 | Japan . |
| 0152979 | 8/1985 | Netherlands . |
| PCT/US90/-00394 | 1/1990 | PCT Int'l Appl. . |
| 0160768 | 4/1984 | Switzerland . |

OTHER PUBLICATIONS

R. A. Peura and Y. Mendelson, "Blood Glucose Sensors: An Overview", IEEE/NSF Symposium on Biosensors, pp. 63–68 (1984).

Primary Examiner—Lee S. Cohen
Assistant Examiner—Kevin Pontius
Attorney, Agent, or Firm—Hamilton, Brook, Smith & Reynolds

[57] ABSTRACT

To determine glucose or other constituents of the human or animal body, a stabilized near-infrared radiation beam containing two alternating wavelengths that have approximately equal extinction coefficients in the tissue, is directed onto the sample area, the transmitted signal alternating component is zeroed by tuning one of the wavelengths, the extracellular-to-intracellular fluid ratio of the tissue is changed by exerting varying mechanical pressure on the tissue, or the ratio is allowed to change as a result of the natural pulsation. The alternating component of the transmitted beam power is measured in the changed fluid ratio state. The amplitude of the alternating-current (AC) signal given by the detector, is taken to represent glucose concentration or the difference from a preset reference concentration.

20 Claims, 2 Drawing Sheets

U.S. PATENT DOCUMENTS

| | | | |
|---|---|---|---|
| 4,513,751 | 4/1985 | Abe et al. | 128/2 R |
| 4,570,638 | 2/1986 | Stoddart et al. | 128/665 |
| 4,586,513 | 5/1986 | Hamagur | 125/633 |
| 4,603,700 | 8/1986 | Nichols et al. | 128/633 |
| 4,621,643 | 11/1986 | New, Jr. et al. | 128/633 |
| 4,653,498 | 3/1987 | New, Jr. et al. | 128/633 |
| 4,655,225 | 4/1987 | Dahne et al. | 128/633 |
| 4,704,029 | 11/1987 | Van Heuvelan | 356/39 |
| 4,725,147 | 2/1988 | Stoddart | 356/433 |
| 4,750,496 | 6/1988 | Reinhart et al. | 128/635 |
| 4,759,369 | 7/1988 | Taylor | 128/633 |
| 4,768,516 | 9/1988 | Stoddart et al. | 128/665 |
| 4,796,636 | 1/1989 | Branstetter et al. | 128/33 |
| 4,805,623 | 2/1989 | Jobsis | 128/633 |
| 4,817,623 | 4/1989 | Stoddart et al. | 128/665 |
| 4,832,484 | 5/1989 | Aoyagi et al. | 356/41 |
| 4,863,265 | 9/1989 | Flower et al. | 356/41 |
| 4,882,492 | 11/1989 | Schlager | 250/346 |
| 5,028,787 | 7/1991 | Rosenthal et al. | 250/341 |

Fig. 1

ELECTROMAGNETIC METHOD AND APPARATUS TO MEASURE CONSTITUENTS OF HUMAN OR ANIMAL TISSUE

RELATED APPLICATIONS

This is a continuation-in-part of co-pending application U.S. Ser. No. 07/527,514 filed May 23, 1990, now U.S. Pat. No. 5,099,123 entitled "Method for Determining by Absorption of Radiations the Concentration of Substances in Absorbing and Turbid Matrices" claiming priority to EPA 89810382.5 filed May 23, 1989, and U.S. Ser. No. 07/511,229 filed Apr. 19, 1990, now U.S. Pat. No. 5,137,023 entitled "Method and Apparatus for Monitoring Blood Analytes Noninvasively by Pulsatile Photoplethysmography", and U.S. Ser. No. 07/511,341 filed Apr. 19, 1990, now U.S. Pat. No. 5,110,124 entitled "Measuring the Concentration of Absorbing Substances".

Also, a U.S. patent application Ser. No. 07/725,502 entitled "Electromagnetic Method and Apparatus to Measure Constituents of Human or Animal Tissue" has been filed concurrent with this application. All of the above-referenced patent applications are hereby incorporated by reference.

BACKGROUND OF THE INVENTION

This invention relates to the non-invasive measurement of the concentration of substances that absorb electromagnetic radiation, such as light or infrared radiation, in absorbing and turbid matrices, such as human or animal body tissue, using a probe beam of electromagnetic radiation. The invention is described as applied to the special case of glucose measurement in human tissue using near-infrared radiation. It is, however, generally applicable to measurements of the concentration of any species that absorbs electromagnetic radiation, especially in strongly absorbing and turbid matrices.

The infrared measurement methods known in the art are not well adapted to the problem of quantifying an analyte dissolved in a strongly absorbing solvent. The known methods include separate or directly alternating measurements at a "glucose" wavelength and at a "reference" wavelength, where glucose does not absorb, as well as differential wavelength modulation about a glucose absorption band (C. Dahne, D. Gross, European Patent 0 160 768 and references therein). In the known methods, the signal is easily lost into the variable and strong background presented by water and other constituents in the tissue and in the capillary blood flow.

SUMMARY OF THE INVENTION

The present invention is an improvement over co-pending European Patent Application 89810382.5 (Harjunmaa), U.S. Ser. No. 07/527,514 referenced above. In Harjunmaa, a balanced differential modulation method is disclosed wherein a radiation beam comprised of alternating pulses of two wavelengths forming a combined beam, is balanced or nulled using a reference detector that takes a sample of the combined beam before it enters the tissue and is detected by a primary detector. Although suitable for the purposes intended, the precautions taken to deal with the unavoidable differences in the spectral response between the reference detector and the primary detector make the system somewhat complicated.

The balanced differential (or balanced bridge) method of Harjunmaa utilizes two wavelengths that have the special property of having identical extinction coefficients in the sample matrix. A radiation beam is generated that contains these two wavelengths in alternate succession at a suitable frequency. When the beam is properly balanced for the measurement, a detector placed to detect radiation transmitted or reflected by the sample does not detect any alternating component in the radiation; when the sample is inserted into the beam path, the same detector also would detect no alternating component, if the matrix do not contain any of the analytes. Only in the case where there is some analyte in the sample matrix will the detector detect an alternating signal synchronous to the wavelength alternation. This feeble alternating signal is amplified and is then detected using a phase-sensitive detector (or lock-in amplifier).

In the method and apparatus of the present invention, the concentration measurement is accomplished using a two-wavelength alternating radiation probe beam which interacts with the tissue. One of the wavelengths is tunable to account for the expected variability of the background spectrum. Detected signals from the probe beam after passing through the matrix are balanced or nulled with a given unknown reference concentration of analyte present by tuning the variable wavelength beam over a range of frequencies. Next, the fluid balance of the tissue in the radiation beam is changed thereby changing the ratio of the analyte concentration to the reference concentration. The alternating component of the interacted probe beam is then detected. The amplitude of the alternating-current (AC) signal given by the detector represents analyte concentration or the difference from a preset reference analyte concentration. The interaction of radiation with tissue can occur in either a reflecting or transmissive mode.

BRIEF DESCRIPTION OF THE DRAWINGS

FIG. 1 is a block diagram of the apparatus of the invention.

DETAILED DESCRIPTION OF THE INVENTION

Figure 1:
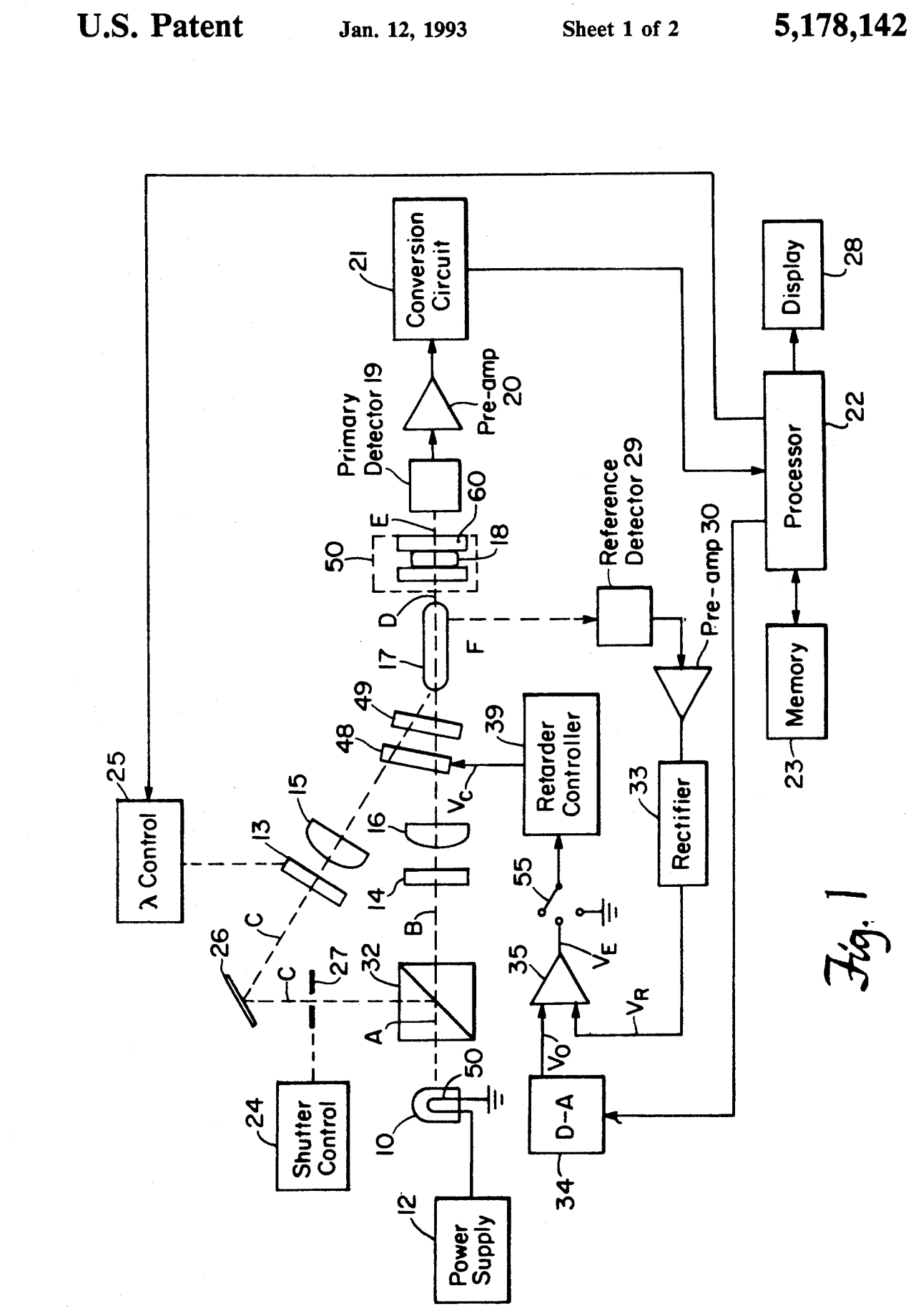
Figure 2:
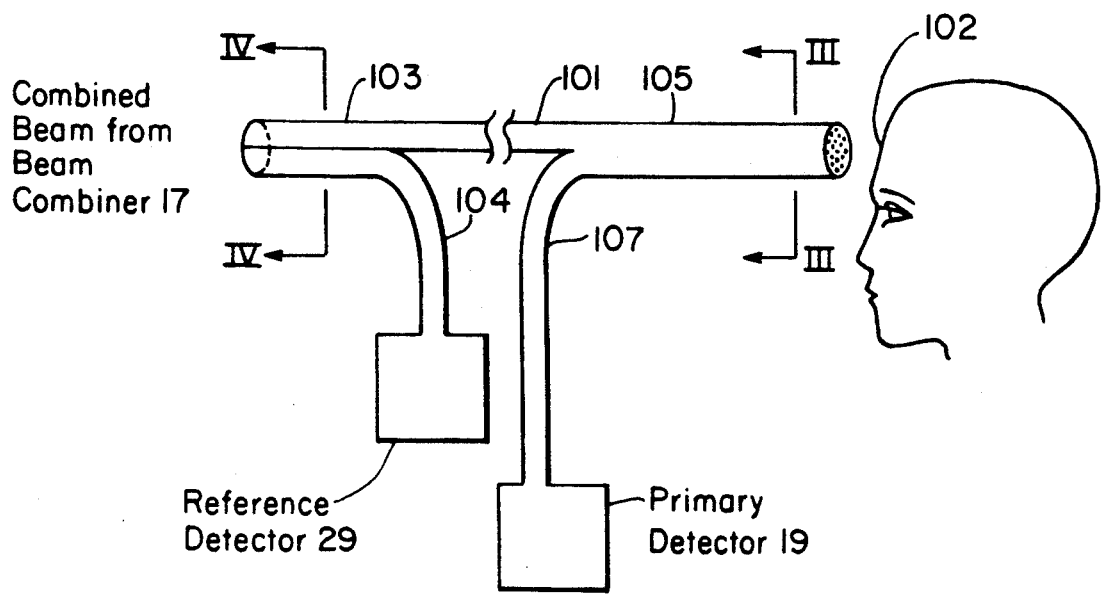
FIG. 2 is a side view of a measuring head for use with the apparatus of FIG. 1 in a reflective mode of operation.

Referring now to FIG. 1 the invention will now be described in detail in connection therewith.

A light source 10 generates a beam A of electromagnetic energy or radiation preferably in the infrared range of the light spectrum. Preferably, the intensity of the beam A is maintained constant by power supply 12 coupled to lamp filament 50. Beam A is split into two beams, B and C, of equal intensity using polarizing beam splitter 32. Beam C is reflected by mirror 26. Both beams B & C are directed through respective interference filters 14 and 13 and focusing lenses 16 and 15, toward optical beam combiner 17.

Filters 14 and 13 are used to select the preferred wavelengths for beams B and C respectively. In the present system, the wavelength $\lambda_1$ for the constant wavelength beam B is at 1600 nm while the center wavelength $\lambda_2$ of the variable wavelength beam C is at 1750 nm. The wavelength of beam C is varied by control 25 which mechanically tilts filter 13 to move the wavelength $\lambda_2$ of the beam C to shorter wavelengths.

These wavelengths are specifically selected for glucose concentration determination since glucose absorbs at 1600 nm and glucose absorption is substantially less and fairly constant in the range of 1670–1730 nm.

To select one of the wavelengths at a time, the two constituent beams B and C are directed at a liquid crystal variable retarder 48. It is controlled electrically, by a control voltage Vc from controller 39, to alternate between two states: nonrotating and rotating. After the retarder the beams encounter a sheet polarizer 49. Its function is to transmit only one linear polarization component. The rotator will either do nothing or rotate both constituent beam polarizations about 90 degrees. Thus, either one or the other constituent beam will be transmitted, alternating at the amplitude modulation frequency of the AC controlling voltage Vc. The retarder 48 also controls the intensity relation of the two wavelength half-periods by producing elliptically polarized intermediate states, according to the control voltage Vc, and thereby causing reduced transmittance of the given constituent beam through the polarizer 49. In that case, there will be a corresponding residual transmittance for the other constituent beam. This residual transmittance has no effect on the operation of the system since only the AC component of the beam intensity is detected.

The two beams B and C are combined in a beam combiner 17 which may comprise a tapered aluminum tube having a polished interior surface. A glass rod could also be used, as well as an integrating sphere or film optics. A portion F of the combined beam is sampled by a reference detector 29 through a hole drilled in the side of the beam combiner 17.

A main portion of the combined beam D enters a sampling area 18 of the body, such as a fingerweb or an earlobe and is attenuated by the body tissue. The resultant beam E is detected by a photoconductive lead sulfide (PbS) infrared primary detector 19 operating at room temperature. It is important that the two detectors 19 and 29 be closely similar in properties to minimize the offset between them that exists even when they are detecting the same beam. Their spectral sensitivity peaks at about 2.2 . . . 2.5 micrometers. The PbS detectors are operated in bolometer circuits, AC-coupled to preamplifiers 20 and 30. Any other detector sensitive in the relevant wavelength range could be used, with the appropriate coupling and amplifying method.

The primary detector preamplifier 20 is connected to a conversion circuit 21 that phase-sensitively rectifies the analog signals produced by the preamplifier and converts them into digital form. The conversion circuit is connected to a computer processor 22. The processor has at its disposal a memory 23 and a display unit 28.

The reference detector preamplifier is connected to a phase-sensitive rectifier circuit 33 which generates a signal $V_R$ indicative of the difference between the intensities of beams B and C. There is also provided a D/A-converter 34 in which the processor 22 sets the previously recorded offset analog voltage value Vo between the two detectors for the current wavelength. The voltage outputs of the phase-sensitive rectifier and of the D/A-converter are fed to a difference amplifier 35 that provides an error signal $V_E$ to the variable retarder controller 39.

In this example, the measurement is performed on the fingerweb. For that purpose there is provided an adjustable gap mechanism 60 where the fingerweb is inserted for measurement. A temperature control mechanism 50 maintains the sample temperature uniform at body temperature during measurement.

A shutter mechanism 27 is provided to interrupt one of the constituent beams for intensity calibration purposes as explained below.

A glucose determination consists of three steps, called the equalizing, balancing and measuring steps:

An equalizing step is performed preferably before every measurement. During equalization, the sample 18 is not in the beam path. For equalization to begin, the filter 13 is tilted to one extreme of its wavelength range by control mechanism 25. If there is any AC signal output from the primary detector, the output of D/A-converter 34 is changed by processor 22 which in turn causes controller 39 to generate a control voltage Vc which varies the intensity relation between the two alternating beams C and B until a zero primary detector signal output is obtained. The wavelength tuning range is now scanned from end to end by tilting filter 13. At suitable intervals, the offset value Vo required at D/A-converter 34 to bring the output of the primary detector 19 to zero is recorded in memory. This completes the equalization step.

To perform the balancing step, the sample area 18 or fingerweb is introduced between the beam D and the detector 19 in the adjustable gap mechanism 50. The mechanism 50 gently squeezes the web, reducing the thickness of the tissue in the optical path. To avoid hurting the subject, there is a preset maximum pressure at which the squeezing stops even if the target thickness has not been reached. The wavelength tuning range is again scanned, until the alternating signal in the primary detector 19 vanishes. Continuously during this operation, the processor, as it changes the wavelength, also updates the offset voltage in the D/A-converter 34 to reproduce the condition that, in the equalizing step, gave a zero primary detector signal output. When the balancing wavelength is found, scanning is stopped, but the reference detector 29 continues to control the intensity relation and will do so throughout the measuring step.

As the wavelength is changed, the sensitivity of the system to glucose will also change slightly. This is compensated for by reading the correct sensitivity coefficient from a look-up table in the memory. The coefficients are obtained through previous calibration at each wavelength (as described below).

On the basis of the known properties of the instrument, it is known approximately how large the single-wavelength signal amplitude is at a given sample thickness. This information is needed to obtain a quantitatively correct glucose concentration reading, since the alternating signal amplitude obviously scales with the said amplitude. To improve the accuracy of the result, the closed-loop control is disabled by grounding switch 55 so that the output of controller 39 does not change. One constituent beam C is blocked with shutter mechanism 24 and the amplitude of the transmitted single-wavelength beam B is measured, and used to normalize the alternating signal result by division.

To perform the measuring step, the adjustable gap mechanism 50, under processor command, now releases the squeeze or vise 60 on the fingerweb 18, increasing the thickness of tissue in the optical path by a predetermined amount. The material added into the beam path is mostly blood. The optimum thickness increase depends on the wavelengths used. Preferably, it is equal to one attenuation length in the added tissue. One attenuation length is the length in which the power of the probe beam D is attenuated to 0.368 times its original value. Blood has a differential absorbance different from that of the background tissue, thus the signal at the primary detector 19 departs from zero as the tissue thickness is increased. The resultant primary detector output signal is proportional to the differential absorbance and thus to glucose concentration. The result is displayed in the display unit 28.

To improve the stability of the readings, the thickness change may be made cyclical at a frequency in the order of 1 to 10 Hz, after balancing is first accomplished with stationary squeezed tissue. Then the amplitude of the rectified signal form the primary detector represent the analyte concentration, and the eventual drift of the rectified signal in the squeezed state will have less effect on the result.

If during the balancing operation, the correct balance is not found due to the balancing wavelength being outside the wavelength tuning range, the processor displays a message declaring the sample out of range.

Figures 3, 4:
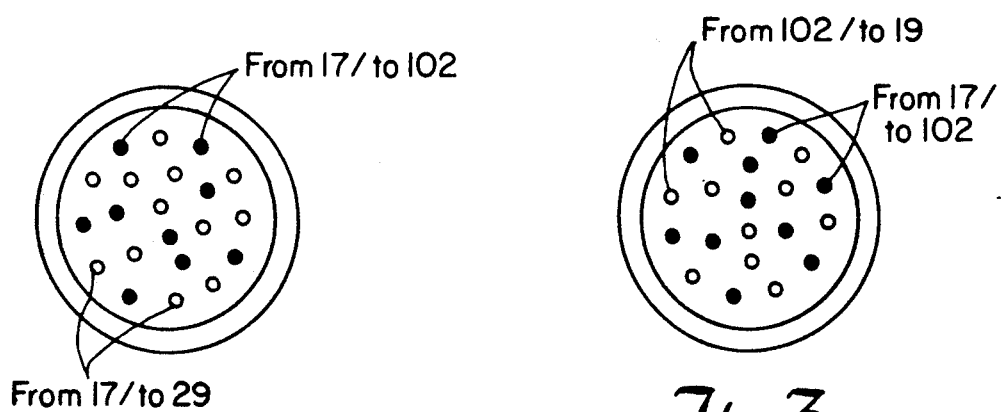
FIG. 3 is a sectional view taken along lines III—III of FIG. 2.
FIG. 4 is a sectional view taken along lines IV—IV of FIG. 2.

FIG. 2A depicts a measuring head useful for operation in the reflective mode. The head 100 comprises a mixed optical fiber bundle 101 that is pressed against the forehead 102 of the subject for the balancing step and then released, while maintaining contact with the skin, to take the glucose reading. The combined beam D emerging from the beam combiner 17 is introduced into the fiber bundle transmitted leg 103. A bifurcation 104 diverts a portion of the infrared beam energy to the reference detector 29. For equalizing, the measuring end of the bundle 105 is pressed against a spectrally substantially neutral equalizing reflector (not shown) that diffuses a portion of the radiation into the receiving bifurcation 107 and on to the primary detector 19. The fibers in both common ends of the bundle are in a mixed arrangement as shown in the sectional views of FIGS. 3 and 4 wherein some of the fibers F couple the light beam from 17 to detector 29 (shown in dark cross-section) and others couple the light beam from 17 to sample tissue on the forehead 102 of the subject or patient. There is no glass cover or window in the measuring end of the bundle; therefore direct reflection from the skin surface is excluded, because any path that leads from the transmitting fibers to the receiving fibers passes through the tissue. Direct reflection is unwanted, because the radiation reflected directly is much stronger than the radiation scattered inside the tissue, and would mask the weak signal obtained from subcutaneous tissue. For balancing, the measuring end is pressed against the forehead 102 and the correct reference wavelength is found. To change the fluid ratio in the forehead skin, the measuring end is slightly released and then the glucose reading is taken.

In the method of this invention, the correct reference wavelength, i.e. the one that has an extinction coefficient equal to that of the primary wavelength, is found by zeroing the AC signal with the tissue background included. The glucose measurement is achieved by modifying the extracellular/intracellular fluid ratio in the tissue and then taking an imbalance reading. If the fluid ratio change is brought about by changing the thickness of tissue between parts of the measuring head, the change of tissue thickness can be either positive or negative. A positive change, or a thickness increase, is preferred, because in that case the balancing can be done under conditions of a larger signal-to-noise ratio, as more transmitted power is available when the thickness is smaller. The thickness change can be made once or many times cyclically to improve signal-to-noise ratio by averaging.

The balancing done with the tissue sample already in the radiation beam cancels errors due to the skin surface and to the tissue in the radiation path, including errors caused by an unknown tissue temperature. No prior knowledge of the balancing wavelength is needed, as long as it is within the tuning range. A reference detector is provided to cancel errors due to variations in the beam intensity relation, which are chiefly due to changes in the lamp spectral output during the measurement. The balancing done in accordance with this invention will also cancel the errors due to the fact that measurements made at different times, although intended to be done at exactly the same measuring site are, in practice, done at slightly different sites. The method according to this invention is sensitive only to the variable component of the tissue as its fluid ratio is changed. The unavoidable differences between the spectral sensitivities of the principal detector and the reference detector, as well as the nonneutrality of the beam sampling for the reference detector, are compensated for by suing a special equalizing procedure.

As explained in Harjunmaa above, the signal obtained in a balanced differential measurement, when taken as a function of the path length in the sample, has a maximum value at a certain path length, which turns out to be the inverse of the extinction coefficient of the sample matrix, or one attenuation length. The extinction coefficient is the sum of the absorption and scattering coefficients. At wavelengths over 2000 nm, water absorbs so strongly that the optimum thickness is much less than 1 mm, a thickness difficult to obtain by squeezing any part of the human body without causing pain. The incremental balanced differential modulation method disclosed here makes it possible to obtain the maximal signal by letting the thickness increment be equal to the optimum path length, while at the same time using a total sample thickness more comfortable to the subject. Also, as the absorption coefficient may be different for different tests that have to be carried out at different wavelengths, it is easy to vary the thickness incremental accordingly.

It is to be noted that scattering by tissue is, at these wavelengths, comparable in magnitude to absorption as an extinction mechanism and causes the resultant extinction coefficient to be much larger than the water absorption coefficient alone.

The interfering substances present in the body may, even after a careful wavelength selection, produce a residual signal due to their differential absorbance. Because of this, a personal calibration step is required before this system is used for absolute glucose determination. The calibration is performed by taking a blood sample of the subject, determining its glucose content and at the same time performing a measurement according to this method. The signal obtained is recorded to correspond to the actual initial glucose concentration. The varying concentrations can then be later deduced by using the known sensitivity of this system to glucose obtained by measuring glucose calibration samples.

If it is judged necessary to improve the specificity of the method, more than one wavelength pair can be used. If, for example, two wavelength pairs are used, the measurement can be done in a sequential mode, where a complete measurement is made according to this disclosure, first using one wavelength pair, and then the wavelengths are changed and another measurement is made with those wavelengths. It is also possible, although it may lead to a more complicated apparatus, to multiplex more than two wavelengths into one measuring beam and then to extract the information pertaining to each wavelength pair from the multiplexed signal. Also, if more than one wavelength pair is used, at least one of the wavelengths may be common to more than one pair.

It is known that, whereas extracellular fluid, which includes interstitial fluid and blood, has a certain glucose concentration, intracellular fluid contains very little glucose, since the latter is consumed inside the cells. Changing the ratio of extracellular to intracellular fluid thus provides a means to modulate the tissue, or by artificial means, such as squeezing the tissue either between the transmitter and receiver parts of measuring head (in the transmission mode) or between a combined transmitter receiver and a suitable bone within the body, such as the forehead.

Equivalents

Those skilled in the art will recognized, or be able to ascertain, using no more than routine experimentation, many equivalents to the specific embodiments of the invention described herein.

The concentration of homologous analytes, such as cholesterol or glucose, may be measured as described herein. Furthermore, the concentration of heterologous analytes, such as alcohol, nicotine, or other drugs, along with materials, such as heavy metals, may be measured in accordance with the invention.

The wavelengths should be selected according to the principle of identical background extinction and simultaneous differential analyte absorption. Usually, an analyte has many absorption bands, among which the selection can be made, with the additional constraints of avoiding interfering substances and, where needed, using more than one wavelength pair to correct for interferences. Wavelengths from the ultraviolet through the visible to the infrared can be used. The wavelength pair intervals of 2125-2185 nm and 2240-2300 nm, or 1550-1650 nm and 1650-1800 nm, are preferable for glucose measurement, with the first noted pair selected for its special property of providing approximate simultaneous balance for water and proteins. The wavelengths of the second noted pair are situated in a wavelength range where water absorption is less than in the range of the first pair, and thus provides for easier implementation of the method because of larger signal levels.

These and all other equivalents are intended to be encompassed by the following claims.

We claim:

1. Non-invasive method for measuring the concentration of predetermined analytes in living body tissue, comprising the steps of:
   a) generating a combined beam of electromagnetic radiation comprised of alternate and repetitive periods of radiation having different wavelengths, the two wavelengths having different absorption coefficients for the analyte being sought, at least one of the wavelengths being tunable, and the repetitive periods forming a measurement cycle;
   b) detecting the combined beam with a primary detector for generating a primary electrical signal proportional to the intensity of the combined beam;
   c) detecting the combined beam with a reference detector for generating a reference signal proportional to the intensity of the combined beam and wherein the electrical response generated by the two period radiations in both detectors is substantially equal in magnitude, thus producing a substantially zero alternating component in the signals of both detectors,
   d) directing the combined beam on the subject tissue so that radiation transmitted or reflected by the tissue reaches the primary detector;
   e) controlling the intensity relation between the periods using the reference signal and tuning the wavelength of one of the periods to obtain a substantially zero alternating component in the primary signal;
   f) changing the ratio of extracellular fluid content to intracellular fluid content in the tissue; and
   g) using the change in the primary signal produced by the principal detector as a result of the fluid ratio change to measure the concentration of the analyte in the tissue.

2. The method according to claim 1, where the combined beam passes through the tissue before being detected by the primary detector.

3. The method according to claim 2, wherein the fluid ratio change comprises change in tissue thickness.

4. The method according to claim 3, wherein the tissue thickness change is substantially equal to the inverse of the extinction coefficient of the tissue at the wavelengths used.

5. The method according to claim 3, wherein the tissue thickness change is repeated cyclically, and the primary signal variation over the cycle is used as a measure of the concentration of the analyte in blood.

6. The method according to claim 1, wherein changing the fluid ratio is achieved by applying pressure on the surface of the tissue.

7. The method according to claim 1, wherein the fluid ratio change is caused by the natural pulsation due to the heartbeat, and the measurement cycle is synchronized to such pulsation.

8. The method according to claim 1 wherein the analyte is a homologous body material, and the wavelengths are within the range of 1 to 2.5 micrometers.

9. The method according to claim 1 for measuring glucose concentration in human or animal body tissue and having one of the wavelengths selected from the interval 2125-2185 nm and another one from the interval 2240-2300 nm.

10. The method of claim 1 wherein the analyte is glucose and one of the wavelengths is selected from the interval 1500-1650 nm and another one is from the interval 1650-1800 nm.

11. The method of claim 1, where the measurement is repeated using one or more additional wavelength pairs and the desired result is obtained from the signal values at each wavelength pair using a mathematical transformation.

12. The method of claim 1, where, before the combined beam is directed on the tissue, the primary and reference detector are equalized by controlling the intensity relation of the different wavelength periods so as to continually produce a minimum alternating signal from the primary detector, tuning the tunable wavelength over the tuning range and at the same time recording into a memory, as a function of the wavelength, a control signal required to produce said minimum alternating signal condition.

13. The method of claim 1 in which calibration is performed while the tissue is in the radiation beam, by blanking one of a pair of wavelength periods and measuring the resulting transmitted alternating single-wavelength signal amplitude and using the measured amplitude to normalize the change in the primary signal.

14. Apparatus for non-invasive measurement of the in vivo concentration of a predetermined analyte in bodily tissue comprising:
   a) radiation means to generate an electromagnetic radiation probe beam containing two alternating wavelength portions where at least one of the wavelengths is tunable and the intensity of the radiation during at least one wavelength portion is controllable,
   b) optical means to transmit the beam to the tissue;
   c) reference detector means to detect a representative portion of the beam, prior to interaction with the tissue, and for generating a reference signal proportional to probe beam intensity;
   d) primary detector means to detect at least a portion of the beam radiation after interaction with the tissue and for generating a primary signal proportional to interacted probe beam intensity;
   e) electrical means to produce an off-set signal in response to the primary signal;
   f) electrical means to produce a control signal from the reference signal and the off-set signal;
   g) control means to control the intensity relation of the alternating portions of the probe beams, according to said control signal,
   h) computing means to convert the primary signal to the concentration value of the analyte sought.

15. Apparatus according to claim 14, wherein the optical means includes means to collect the beam after interaction with the tissue to form an image on the primary detector of the area where the probe beam exits the tissue.

16. Apparatus according to claim 15, wherein the optical means comprises an optical fiber.

17. Apparatus according to claim 16 wherein the optical fiber is bifurcated at a proximal end with a first plurality of fibers for coupling the beam to the reference detector means and a second plurality of fibers for coupling the beam to the tissue for interaction and is bifurcated at a distal end with a third plurality of fibers for coupling the interacted beam to the primary detector means.

18. Non-invasive apparatus for measuring the concentration of predetermined analytes in living body tissue, comprising:
   a) transmission means for generating a combined beam of electromagnetic radiation comprised of alternate and repetitive periods of radiation having different wavelengths, the two wavelengths having different absorption coefficients for the analyte being sought, at least one of the wavelengths being tunable;
   b) a primary detector means for detecting the combined beam before and after interacting with the tissue and for generating a primary electrical signal proportional to the intensity of the combined beam before and after said interaction;
   c) a reference detector means for detecting the combined beam for generating a reference signal proportional to the intensity of the combined beam and wherein the electrical response generated by the two period radiations in both detectors is substantially equal in magnitude, thus producing a substantially zero alternating component in the signals of both detectors,
   d) coupling means for directing the combined beam onto the subject tissue so that radiation transmitted or reflected by the tissue is coupled to the primary detector means;
   e) control means for controlling the intensity relation between the radiation periods in response to the reference signal to tune the wavelength of one of the periods to obtain a substantially zero alternating component in the primary signal;
   f) change means for changing the ratio of extracellular fluid content to intracellular fluid content in the tissue; and
   g) display means responsive to the change, in the primary signal produced by the primary detector means as a result of the fluid ratio change to measure the concentration of the analyte in the tissue.

19. Apparatus according to claim 18, wherein the means for directing directs the combined beam through the tissue before being detected by the primary detector means.

20. Apparatus according to claim 18, wherein the change means comprises means for changing the thickness of the tissue.

* * * * *

UNITED STATES PATENT AND TRADEMARK OFFICE
CERTIFICATE OF CORRECTION

PATENT NO. : 5,178,142

DATED : January 12, 1993

INVENTOR(S) : Hannu Harjunmaa, Yitzhak Mendelson and Yi Wang

It is certified that error appears in the above-identified patent and that said Letters Patent is hereby corrected as shown below:

On the title page:

Item [56]-3rd document listed, delete "5/1890" and insert --5/1990--.

Signed and Sealed this

Eleventh Day of January, 1994

*Attest:*

BRUCE LEHMAN

*Attesting Officer*    Commissioner of Patents and Trademarks